United States Patent
Mandal et al.

(10) Patent No.: US 9,719,965 B2
(45) Date of Patent: Aug. 1, 2017

(54) MUD SETTLEMENT DETECTION TECHNIQUE BY NON-DESTRUCTIVE ULTRASONIC MEASUREMENTS

(71) Applicant: Halliburton Energy Services, Inc., Houston, TX (US)

(72) Inventors: Batakrishna Mandal, Missouri City, TX (US); Shubhajit Ghosh, Sugar Land, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/907,982

(22) PCT Filed: Mar. 16, 2015

(86) PCT No.: PCT/US2015/020753
§ 371 (c)(1),
(2) Date: Jan. 27, 2016

(87) PCT Pub. No.: WO2016/148684
PCT Pub. Date: Sep. 22, 2016

(65) Prior Publication Data
US 2017/0038339 A1 Feb. 9, 2017

(51) Int. Cl.
*G01N 29/024* (2006.01)
*G01N 29/032* (2006.01)
(Continued)

(52) U.S. Cl.
CPC .......... *G01N 29/024* (2013.01); *G01N 29/02* (2013.01); *G01N 29/4409* (2013.01);
(Continued)

(58) Field of Classification Search
CPC .............. G01N 29/024; G01N 29/032; G01N 29/4427; G01N 29/4454; G01N 2291/011;
(Continued)

(56) References Cited

U.S. PATENT DOCUMENTS 4,377,087 A * 3/1983 Rodot .................. G01N 29/024
73/594
4,522,068 A 6/1985 Smith
(Continued)

FOREIGN PATENT DOCUMENTS

CN 101614648 A 12/2009
CN 203551430 U 4/2014
(Continued)

OTHER PUBLICATIONS

International Search Report and The Written Opinion of the International Searching Authority, or the Declaration, Dec. 3, 2015, PCT/US2015/020753, 10 pages, ISA/KR.

*Primary Examiner* — Laura Martin
*Assistant Examiner* — Rose M Miller
(74) *Attorney, Agent, or Firm* — Haynes and Boone, LLP

(57) ABSTRACT

Systems and methods of determining settlement characteristics of a drilling mud are disclosed. Conditions under which heavier elements of the drilling mud settle under the influence of gravity can be determined. Samples of drilling mud can be placed in testing cells, and ultrasonic test pulses can be transmitted through the samples. Responses to the test pulses can be detected and compared to other responses detected at different vertical positions within the testing cell. Settlement can be detected when the responses from different vertical positions are generally dissimilar. An environmental temperature of the testing cell can be changed over a testing time interval, and a settlement temperature can be (Continued)

determined by detecting a divergence in the responses from different vertical positions.

19 Claims, 4 Drawing Sheets

(51) Int. Cl.
G01N 29/02 (2006.01)
G01N 29/44 (2006.01)
(52) U.S. Cl.
CPC ... *G01N 29/4427* (2013.01); *G01N 2291/011* (2013.01); *G01N 2291/025* (2013.01); *G01N 2291/02416* (2013.01); *G01N 2291/02836* (2013.01); *G01N 2291/02881* (2013.01)
(58) Field of Classification Search
CPC .......... G01N 2291/02836; G01N 2291/02881; G01N 2291/015; G01N 2291/02416
USPC ...... 73/571, 152.03, 152.04, 152.18, 152.19, 73/597, 598, 645, 646, 573, 594
See application file for complete search history.

(56) References Cited

U.S. PATENT DOCUMENTS

| | | | |
|---|---|---|---|
| 4,770,042 A | 9/1988 | Cobb | |
| 4,814,389 A | 3/1989 | Garvey et al. | |
| 5,563,845 A * | 10/1996 | Walsh | G01F 23/2965 367/7 |
| 6,044,703 A * | 4/2000 | Fay | G01F 23/296 73/290 V |
| 6,176,323 B1 | 1/2001 | Weirich et al. | |
| 6,957,700 B2 | 10/2005 | Mandal | |
| 8,322,198 B2 | 12/2012 | Iverson et al. | |
| 8,752,414 B2 | 6/2014 | Jamison et al. | |
| 2001/0035312 A1* | 11/2001 | Han | E21B 47/101 181/115 |
| 2004/0020294 A1* | 2/2004 | Buckin | G01N 29/036 73/597 |
| 2008/0216577 A1* | 9/2008 | Irani | G01N 29/024 73/597 |
| 2013/0312511 A1 | 11/2013 | Jamison et al. | |
| 2015/0354343 A1* | 12/2015 | Wroblewski | G01N 29/024 73/152.18 |
| 2016/0169839 A1* | 6/2016 | Gottlieb | G01N 29/02 367/7 |

FOREIGN PATENT DOCUMENTS

| | | |
|---|---|---|
| WO | WO 2004/113467 A1 | 12/2004 |
| WO | WO 2013/154435 A1 | 10/2013 |

\* cited by examiner

MUD SETTLEMENT DETECTION TECHNIQUE BY NON-DESTRUCTIVE ULTRASONIC MEASUREMENTS

The present application is a U.S. National Stage patent application of International Patent Application No. PCT/US2015/020753, filed on Mar. 16, 2015, the benefit of which is claimed and the disclosure of which is incorporated herein by reference in its entirety.

BACKGROUND

1. Field of the Invention

The present disclosure relates generally to the testing of fluids to characterize the settlement of relatively heavy components of the fluidr time. More particularly, embodiments of the disclosure relate to systems and methods that employ non-destructive techniques for monitoring drilling mud samples during static aging tests and/or dynamic flow tests.

2. Background

Rotary drilling techniques used in drilling hydrocarbon wellbores commonly employ a drilling fluid or "mud" to provide lubrication to a drill bit and to carry geologic cuttings from the bottom of the wellbore. The mud is generally circulated down-hole into the wellbore through a drill string, out through the drill bit, and then back up to a surface location through an annulus defined between the drill string and a wall of the wellbore. The mud is also relied upon to exert a hydrostatic pressure on the walls of the wellbore to prevent collapse of the wellbore, and to prevent premature entry of formation fluids into the wellbore. The drilling mud may be selected to have a sufficiently high density to control the inflow of formation fluids into the wellbore and sufficiently low density to permit efficient operation of the drill bit.

Often, heavier components of the drilling mud can (end to settle under the influence of gravity to lower regions of the wellbore in a phenomenon commonly referred to "sag." In operation, the "sag" of a drilling fluid could present difficulties in circulating the mud, and can prevent the mud from effectively managing the formation pressures. Thus, the sag characteristics of a particular drilling fluid are often characterized in laboratory conditions prior being deployed in a wellbore. For instance, some laboratory testing involves static aging of samples of the drilling mud at elevated temperatures for a given time period, which could range from about a day to more than about three months. The samples are inspected and evaluated at the end of the time interval to determine the degree to which settlement has occurred. Based on the evaluation, the composition of the drilling mud and/or the temperature at which the drilling mud is statically aged can be adjusted, and then a new sample of drilling mud can re-assessed until a composition suitable for a particular application can be identified. This iterative process can be time consuming may not sufficiently characterize the drilling mud. For example, various operational limits of the drilling mud may not be specifically identified, thus creating challenges for an operator.

BRIEF DESCRIPTION OF THE DRAWINGS

The disclosure is described in detail hereinafter on the basis of embodiments represented in the accompanying figures, in which.

DETAILED DESCRIPTION

Figure 1:
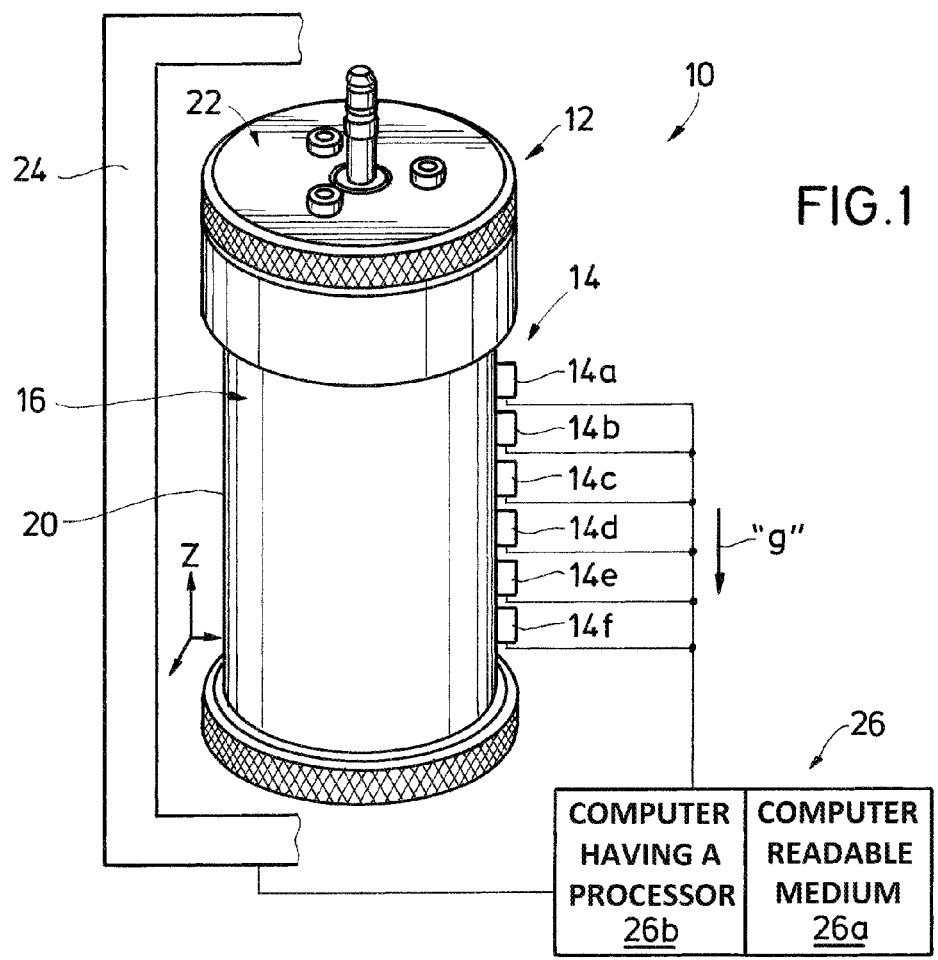
FIG. 1 is a schematic view of a system for use in mud settlement testing operations including an aging cell with a transducer array in accordance with one or more exemplary embodiments of the disclosure.

The disclosure may repeat reference numerals and/or letters in the various examples or Figures. This repetition is for the purpose of simplicity and clarity and does not in itself dictate a relationship between the various embodiments and/or configurations discussed. Further, spatially relative terms, such as beneath, below, lower, above, upper, up-hole, down-hole, upstream, downstream, and the like, may be used herein for ease of description to describe one element or feature's relationship to another element(s) or feature(s) as illustrated, the upward direction being toward the top of the corresponding figure and the downward direction being toward the bottom of the corresponding figure. Unless otherwise stated, the spatially relative terms are intended to encompass different orientations of the apparatus in use or operation in addition to the orientation depicted in the Figures. For example, if an apparatus in the Figures is turned over, elements described as being "below" or "beneath" other elements or features would then be oriented "above" the other elements or features. Thus, the exemplary term "below" can encompass both an orientation of above and below. The apparatus may be otherwise oriented (rotated 90 degrees or at other orientations) and the spatially relative descriptors used herein may likewise be interpreted accordingly.

1. Description of Exemplary Embodiments

Referring to FIG. 1, a system 10 for use in mud settlement testing operations is illustrated n accordance with one or more embodiments of the present disclosure. The system 10 includes an aging cell 12 including a transducer array 14. The aging cell 12 includes a container 16 in which a drilling mud 18 (FIG. 2A) may be maintained for testing. Although the systems and methods described herein are described with reference to drilling mud 18, it should be appreciated that any fluid with solids or other relatively heavy elements intermixed therein can be characterized by the systems and methods. As described in greater detail below, the transducer array 14 is operable to impart energy to the drilling mud 18 (FIG. 2A) to facilitate an assessment of the settlement characteristics of the drilling mud 18. The container 16 includes a vertical wall 20, which is defined along a vertical direction "z" and supports the transducer array 14. The transducer array 14 includes a plurality of distinct transducers 14a through 14f spaced from one another in the vertical direction "z" along the vertical wall 20. As illustrated herein, the aging cell 12 is oriented such that an upper transducer 14a is arranged at an upper end of the vertical wall 20 and a lower transducer 14f is arranged at a lower end of the vertical wall 20. Thus, in the descriptions that follow, gravity acts in the general direction arrow "g" toward transducer 14f.

The transducers 14a through 14f may comprise any type of transducers including, but not limited to, electrical, mechanical, electromagnetic, light energy, acoustic and thermal energy transducers. In some exemplary embodiments, the transducers 14a-14f may comprise ultrasonic transducers that operate in the frequency range of about 250 kHz to about 500 kHz. Each of the transducers 14a-14f can operate in either a pulse echo triode or a pitch catch mode. In the pulse echo mode, each of the transducers 14a-14f operates both as a transmitter and as a receiver, and in the pitch-catch mode, one or more of the transducers 14a-14f operates as a transmitter and one or more of the other transducers 14a-14f or 28a-28f (FIG. 2B) operates as a receiver. In case of ultrasonic transmitters, for example, the transducers 14a-14f may be used to generate a particular acoustic wave pattern, for example to transmit an acoustic wave or test pulse into a particular direction into the drilling mud 18. In case of ultrasonic sensors, the transducers 14a-14f may be used to acquire information about the acoustic wave patterns in a measurement area from the drilling mud 18.

Although in some exemplary embodiments, the transducer array 14 is arranged on an interior of the container 16 or in other locations on the aging cell 12, as illustrated in FIG. 1. the transducers 14a-14f of the transducer array 14 are arranged an exterior of the vertical wall 20. Thus, to impart energy to the drilling mud 18 (FIG. 2A) within the container 16, the transducers 14a-14f transmit energy through the vertical wall 20. The vertical wall 20 can be constructed of materials that permit passage of the type of energy provided by the transducers 14a-14f, without significant attenuation or reflection thereof. For example, in embodiments wherein each of the transducers 14a-14f provides acoustic energy, the vertical wall 20 may be constructed of a thermoplastic material such as polypropylene. The vertical wall 20 is arranged in a generally cylindrical shape, although it should be appreciated that other arrangements, such as rectangular, oblong, etc., are also contemplated. The container 16 is illustrated as including a lid 22 thereon, although in some embodiments, the container 16 may be substantially uncovered.

The system 10 also includes a heater 24 and a controller 26. The heater 24 is selectively operable to increase an environmental temperature of the aging cell 12 through a predetermined schedule during a testing time interval "T" (see FIGS. 4a and 4B). In some exemplary embodiments, the heater 24 comprises an oven, a heat lamp, or other apparatus recognized in the art. In some exemplary embodiments, the controller 26 is operatively and communicatively coupled to both the heater 24 and to the transducer array 14 to provide instructions thereto and to receive feedback therefrom. In other embodiments, the heater 24 can be operated independently from the controller 26. In some embodiments, the controller 26 may include a computer having a processor 26a and a computer readable medium 26b operably coupled thereto. The computer readable medium 26b can include a nonvolatile or non-transitory memory with data and instructions that are accessible to the processor 26a and executable thereby. In one or more embodiments, the computer readable medium 26b is pre-programmed with instructions for causing the heater 24 to increase the environmental temperature of the aging cell 12 along the predetermined schedule, and instructions for causing the transducer array 14 to transmit test pulses and to record and analyze responses to the test pulses as described in greater detail below.

Figures 2A, 2B:
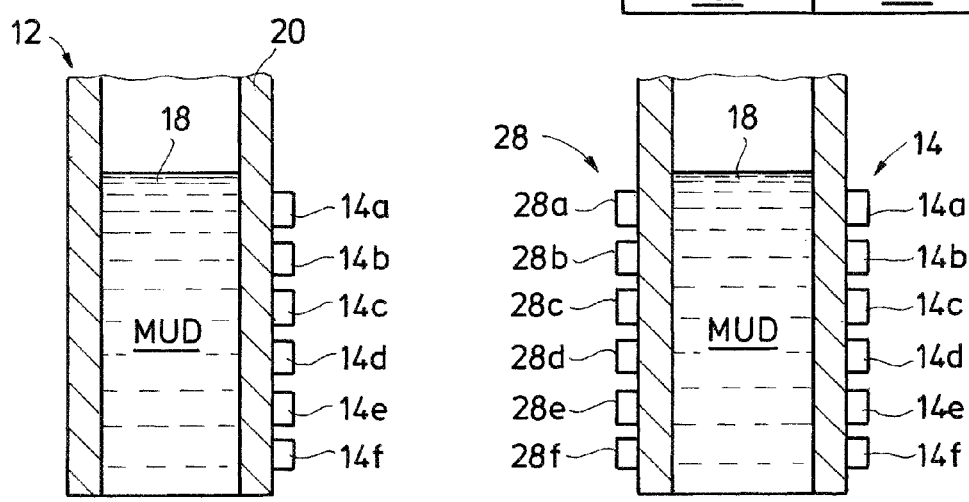
FIG. 2A is a cross-sectional schematic view of the aging cell of FIG. 1.
FIG. 2B is a cross-sectional schematic view of an aging cell having a transducer array and a receiver array in accordance with one or more alternate embodiments of the disclosure.

Referring to FIG. 2A, each of the transducers 14a-14f is generally disposed at the same circumferential position around the vertical wall 20 of the aging cell 12. In other exemplary embodiments, one or more of the transducers 14a-14f may be circumferentially spaced from the other transducers 14a-14f. In some exemplary embodiments, the transducers 14a-14f may comprise any kind of acoustic transducers, including acoustic sensors, acoustic transmitters, and acoustic transmitter-receivers such that the transducers 14a-14f can be operated in the pulse echo and pitch catch modes as described above. The transducers 14a-14f may comprise, piezoelectric transducers, e.g., and at least one of the acoustic transducers 14a-14f may be used to generate particular acoustic wave patterns, e.g., to transmit an acoustic waves into a particular direction into the drilling mud 18. At least an upper transducer, e.g. transducer 14a, and a lower transducer, e.g. 14f may also be used to acquire information about the acoustic wave patterns in a measurement area adjacent the respective transducer, e.g. transducers 14a and 14f. In some exemplary embodiments, each of the intermediate transducers 14b-14e may also be used as sensors to acquire information about the acoustic wave patterns. The transducers 14a-14f can be operable to transmit signals indicative of the acoustic wave patterns to the controller 26 (FIG. 1), where the signals can be recorded an analyzed in real time or subsequent to a testing time interval as described in greater detail below.

In some exemplary embodiments (not shown), the transducer array 14 may be replaced with a single transducer 14a. The single transducer 14a and/or the aging cell 12 can be moved in a controlled manner along the vertical direction "z" such that he single transducer 14a can collect data from a plurality of different depths of the aging cell 12. An automatic positioning system (not shown) may be operably coupled to the controller 26 such that the controller can induce the relative movement of the aging cell 12 and/or the single transducer 14a, and positional information can be recorded and correlated to the data collected.

In some exemplary embodiments, such as those illustrated in FIG. 2B, a transmitting transducer array 28 is arranged to transmit acoustic wave patterns through the drilling mud 18, and the transducer array 14 is arranged to detect the acoustic wave patterns. A test pulse, e.g., an acoustic wave pattern transmitted from a single transmitting transducer 28a, e.g., can be received by each of the receiving transducers 14a-14f across the drilling mud 18. Alternatively or additionally, each transmitting transducer 28a-28f can transmit test pulses directly to a corresponding receiving transducer 14a-14f, respectively, which is disposed at the same vertical position. The acoustic wave patterns received by the transducers 14a-14f in response to the acoustic wave patterns and 24a-24f can be evaluated and compared to one another, as described below, to assess the stability or the settlement characteristics of the drilling mud 18.

Figure 3A:
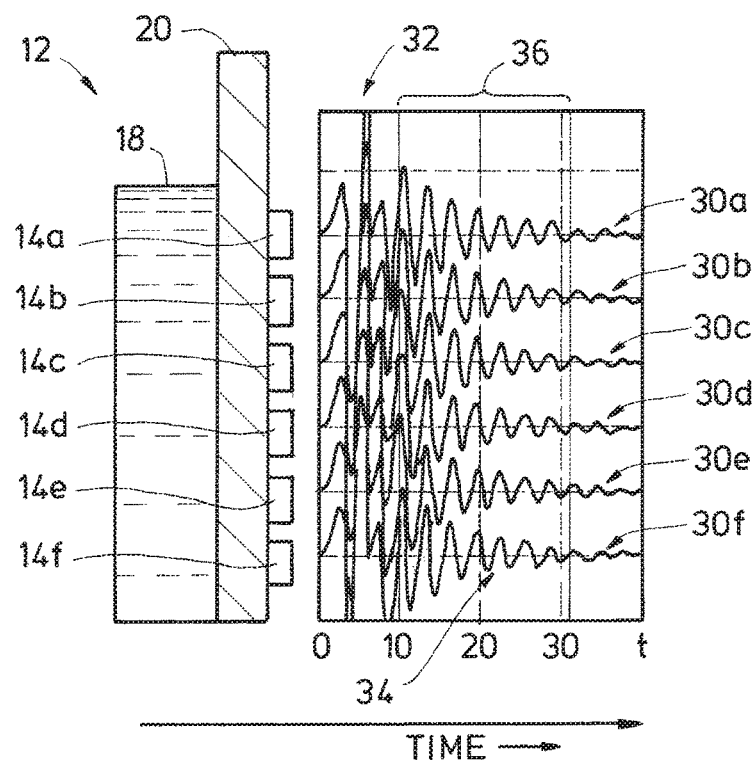
FIG. 3A is a graphical view of a set of transducer response signatures indicative of a set of test pulses generated by the transducer array of FIG. 1 wherein the aging cell contains a drilling mud exhibiting generally stable settlement characteristics.

Referring now to FIG. 3A, a set of transducer response signatures 30a-30f are illustrated. Each transducer response signature 30a-30f represents an acoustic wave pattern received by a respective transducer 14a-14f for a time interval "t." In some exemplary embodiments, the duration of the time interval "t" ranges from about 50 micro-seconds to about several hundred micro-seconds. The time interval "t" begins when a test pulse or a main pulse of energy is imparted to the drilling mud 18 by one or more of the transducers 14a-14f and continues for a predetermined time over which the energy dissipates substantially. In some exemplary embodiments, the main pulse can be imparted simultaneously from each of the transducers 14a-14f to the drilling mud 18, and in some exemplary embodiments, the main pulse can be imparted sequentially from each of the transducers 14a-14f. The response signatures 30a-30f each include a main pulse portion 32 in which the main pulse of energy is received and a ringing or resonance portion 34 that follows the main pulse portion 32. The sample of drilling mud 18 illustrated in FIG. 3A is well mixed and generally uniform throughout the container 16, and thus, the transducer response signatures 30a-30f are also generally uniform.

A monitoring window 36 can be defined within the resonance portions 34 of each of the transducer response signatures 30a-30f. The beginning and ending of the monitoring window 36 can be selected according to any predetermined criteria. In some embodiments, the beginning and ending of the monitoring window 36 can be selected to exclude certain portions of the response signatures 30a-30f, and thereby emphasize any potential differences in the energy detected from each of the individual transducers 14a-14f. Differences in the energy detected from the individual transducers 14a-14f may be indicative of differences in the impedance of the drilling mud 18 at the vertical positions adjacent each of the individual transducers 14a-14f. Thus, the portions of the response signatures 30a-30f that are similar despite differences in the impedance of the drilling mud 18 can be excluded. For example, the beginning of the monitoring window 36 can be selected to exclude the main pulse portion 32 and the ending of the monitoring window 36 may be selected to exclude portions of the response signatures 30a-30f when most of the energy from the main pulse has dissipated. In some embodiments, the monitoring window 36 may begin and end at predetermined times after the main pulse is imparted to the drilling mud 18. In other embodiments, the monitoring window 36 can be dependent on an aspect of one of the individual transducer response signatures 30a-30f. For example, the monitoring window 36 can begin or end when an amplitude of an individual the response signature, e.g., response signature 30a, reaches a predetermined percentage of an amplitude of a maximum amplitude detected during the main pulse portion 32.

Where the transducers 14a-14f are ultrasonic transducers, the monitoring window 36 for each transducer response signatures 30a-30f can be characterized by a characterizing parameter "P" (see FIGS. 4a and 4b), which can include, e.g., any ultrasound parameter including frequency, propagation speed, wavelength, amplitude power or intensity. In some exemplary embodiments, the characterizing parameter "P" can represent the total amount of ultrasonic energy detected by a particular transducer, e.g. transducer 14a, over the corresponding monitoring window 36. Since transducer response signatures 30a-30f depicted in FIG. 3A are generally uniform, the parameter "P" characterizing the monitoring window 36 is generally equivalent for each of the transducer response signatures 30a-30f.

Figure 3B:
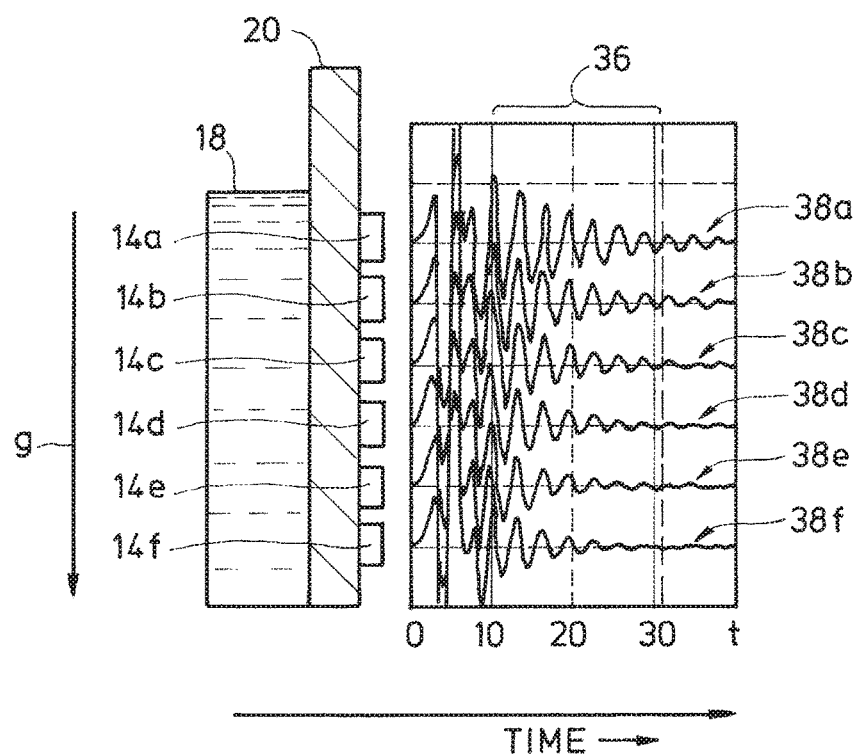
FIG. 3B is a is a graphical view of a set of transducer response signatures similar to FIG. 3A wherein the aging cell contains a drilling mud exhibiting generally unstable settlement characteristics.

Referring now to FIG. 3B, a set of transducer response signatures 38a-38f are illustrated for a sample of drilling mud 18 exhibiting generally unstable settlement characteristics. In particular, the transducer response signatures 38a-38f can represent the energy detected by each of the transducers 14a-14f after a point in an aging response test where the uniformity in the drilling mud 18 has deteriorated, and heavier elements in the drilling mud 18 are deposited toward the bottom of the container 16 (FIG. 1) in the direction of arrow "g." Due to the settlement of the heavier elements, the density drilling mud 18, and correspondingly the impedance of the drilling mud 18, increases in the direction of arrow "g." Since the impedance of the drilling mud 18 adjacent the lowermost transducer 14f is greater than impedance of the drilling mud 18 adjacent the uppermost transducer 14a, the transducer response 38f dissipates more quickly than the transducer response 38a. For example, the amplitude of the waveform 38f is reduced to a particular reference amplitude earlier in the response time interval "t" than the amplitude of the waveform 38a reaches the reference amplitude. The characterizing parameter "P" for the transducer response signature 38f will be dissimilar or divergent from the characterizing parameter "P" for the transducer response signature 38a.

Figure 4A:
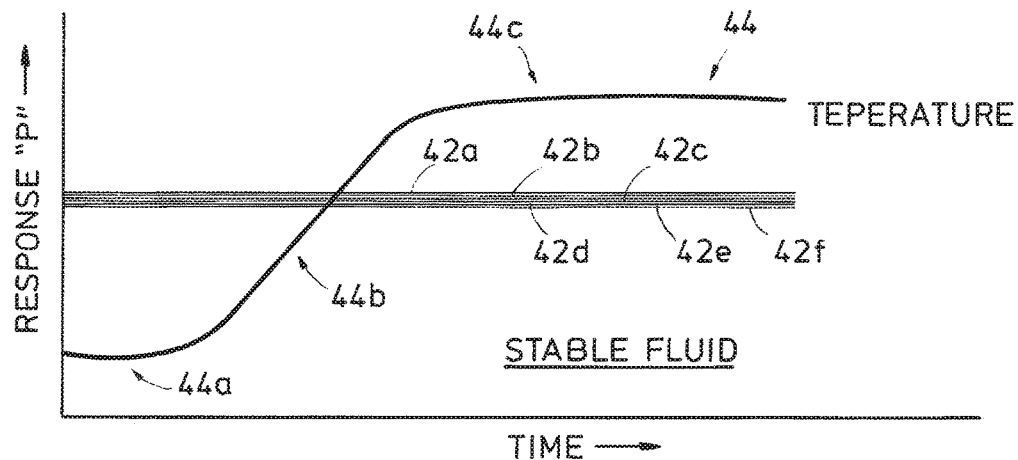
FIG. 4A is a graphical view of a compilation of transducer responses generated over a time interval and an induced temperature change over which the subject drilling mud exhibits generally stable settlement characteristics.

Referring now to FIG. 4A, and with continued reference to FIG. 3A, the characterizing parameter "P" for each transducer response 30a-30f is illustrated on a vertical axis, and a testing time interval "T" is illustrated on a horizontal axis. In some exemplary embodiments, the duration of the testing time interval "T" can be in the range from about a day to more than about three months. Thus, in some embodiments, the testing time interval "T" can include hundreds or thousands of response time intervals "t." In some exemplary embodiments, the response time intervals "t" can spaced at regular intervals throughout the testing time interval "T," e.g., each of the transducers 14a-14f FIG. 3A) can generate a test pulse and record a response every minute or hour. In other exemplary embodiments, the response time intervals "t" may immediately follow one another for the duration of the testing time interval "T." The characterizing parameter "P" for a monitoring window 36 defined in a resonance portion 34 of each transducer response 30a-30f can plotted along the testing time interval "T" to generate fluid response curves 42a-42f. The fluid response curves 42a-42f represent the reaction of the drilling mud 18 at the vertical positions corresponding to the transducers 14a-14f over the testing time interval "T" and the testing conditions under which the aging cell 12 and drilling mud 18 are subject.

In some exemplary embodiments, one of the testing conditions that can be controlled is an environmental temperature under which the drilling mud 18 is maintained. For example, the heater 24 (FIG. 1) can be operated to increase the environmental temperature according to a predetermined schedule as represented by temperature curve 44. In the illustrated embodiment, the predetermined schedule, and thus, the temperature curve 44, includes an initial constant temperature portion 44a, a subsequent increasing temperature portion 44c, and a final constant temperature portion 44c. In other exemplary embodiments, the predetermined schedule can take any form including generally linear, generally constant, generally increasing or generally decreasing according to specific testing requirements of the drilling mud.

The fluid response curves 42a-42f of FIG. 4A represent an aging test of a generally stable drilling mud 18 that remains uniform over the testing time interval "T" and the corresponding change in environmental temperature. Thus, each of the fluid response curves 42a-42f follow the same general path for the testing time interval "T" since the characterizing parameter "P" does not change according to the vertical position in the aging cell 12.

Figure 4B:
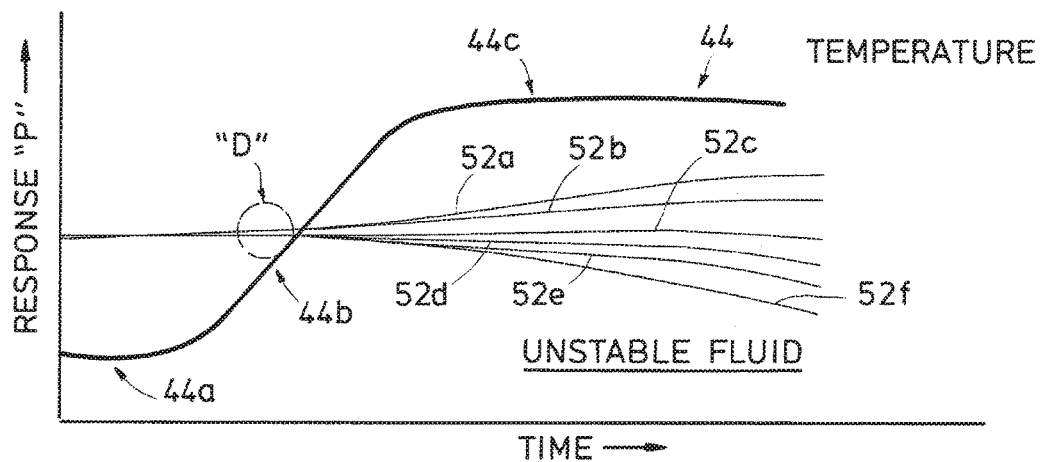
FIG. 4B is a graphical view of a compilation of transducer responses similar to FIG. 4A wherein the drilling mud exhibits generally unstable settlement characteristics.

Referring now to FIG. 4B, and with continued reference to FIG. 3B, fluid curves 52a-52f represent an aging test of a generally unstable drilling mud 18 wherein heavier elements of the drilling mud 18 settle in the direction of arrow "g." initially in the testing time interval "T," e.g., during the initial constant temperature portion 44a of the temperature curve 44, each of the fluid response curves 52a-52f follow same general path. This portion of the fluid response curves 52a-52f indicates that the drilling mud 18 remains well mixed throughout this initial portion of the testing interval.

During the increasing temperature portion 44b of the temperature curve 44, the fluid response curves 52a-52f reach a divergence point "D" in which the response curves 52a-52f separate and generally diverge. In some exemplary embodiments, the divergence point "D" can be defined where the characterizing parameters "P" for the upper and lower vertical locations corresponding to transducers 14a and 14f, respectively, differ from one another more than a predetermined tolerance. The divergence point "D" represents a particular settlement time within the testing interval "T" at which the settlement of the drilling mud 18 is initiated. From the temperature curve 44, a settlement temperature can be determined from the settlement time, which represents the environmental temperature at which the settlement of the drilling mud 18 is initiated. The settlement time and settlement temperature can be employed to inform a drilling operator or a drilling mud designer.

After the divergence point "D," the fluid response curves 52a-52f continue to diverge for the remainder of the testing time interval "T." The extent to which the fluid response curves 52a-52f diverge can characterize the extent o which settlement occurred in the drilling mud over the testing time interval "T."

2. Example Implementation

Figure 5:
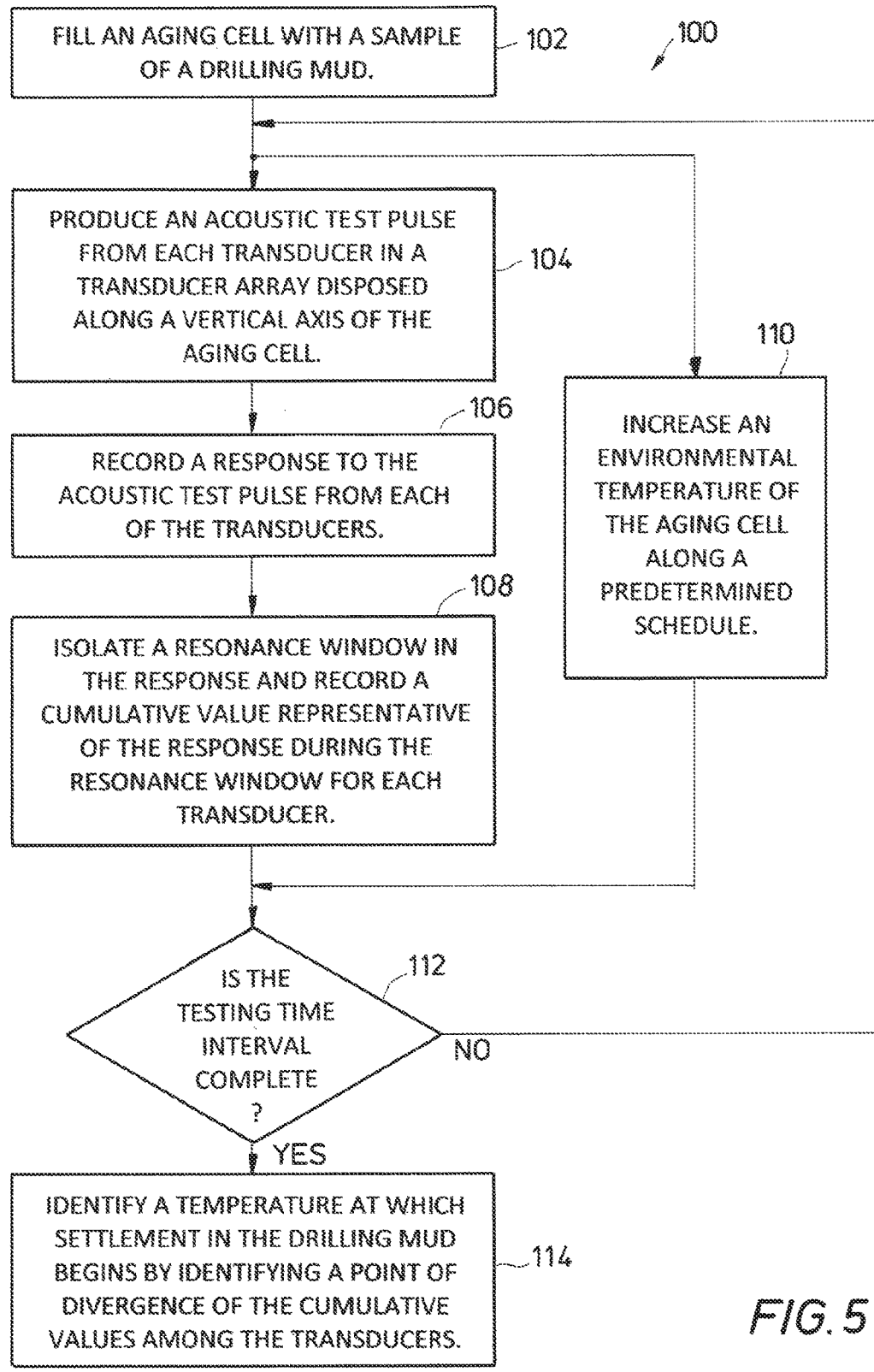
FIG. 5 is a flowchart illustrating testing procedures employing the aging cells and transducer arrays of FIG. 1.

Referring now to FIG. 5, and with reference to FIGS. 1 and 2A, some exemplary embodiments of an aging test procedure 100 are described that employ the testing system 10 described above. Initially at step 102, an aging cell 12 is filled with a sample of drilling mud 18. At step 104, a main acoustic test pulse is generated from each transducer 14a-14f in an array 14 of transducers disposed along a vertical axis of the aging cell 12. In some exemplary embodiments, the computer readable medium 26b can have instructions stored thereon that cause the processor 26a to instruct the transducers 14a-14f to generate a particular acoustic wave pattern to transmit a test pulse into the drilling mud 18 in a particular direction. Thus, transducers 14a-14f serve as transmitters in step 104. As described above, however, the test pulses can be generated from other sources such as transducer array 28 (FIG. 2B). Next, at step 106, the transducers 14a-14f serve as sensors, which detect the response to the acoustic test pulse over a response time interval "t." The resulting transducer response signatures 30a-30f (FIG. 3A) or 38a-38f (FIG. 3B) can be communicated from the transducers 14a-14f to the processor 26a, and the processor 26a can record the response signatures 30a-30f, 38a-38f onto the computer readable medium 26b. The processor 26a can then isolate a monitoring window 36 in a resonance portion 34 of each of the response signatures 30a-30f, 38a-38f (step 108), and determine and record a characterizing parameter "P" of each response signature 30a-30f, 38a-38f.

Simultaneously with steps 104-108, or in some exemplary embodiments, in sequence with steps 104-108, the processor 26a can instruct the heater 24 to alter the environmental temperature of the aging cell 12 and the drilling mud 18 therein along a predetermined schedule at step 110. Next, at decision 112, the processor 26a determines whether the testing time interval "T" is complete. In some embodiments, the duration of the testing time interval "T" is preprogrammed onto the computer readable medium 26b. If the testing time interval "T" is not yet complete, the procedure 100 returns to steps 104 and 110 where additional data can be collected and the aging cell 12 can be maintained according to the predetermined schedule.

If the testing time interval "T" is complete, the procedure 100 proceeds to step 114. The processor 26a determines a divergence point "D" where the characterizing parameter "P" corresponding to an upper vertical location, e.g., the characterizing parameter "P" for response signature 38a, differs from the characterizing parameter "P" corresponding to an lower vertical location, e.g., the characterizing parameter "P" for response signature 38f, by more than a predetermined tolerance. A settlement temperature along the predetermined schedule that corresponds to the divergence point "D" may then be determined.

In some embodiments, the system 10 may then proceed to output the settlement temperature and or other data from an output device (not shown) coupled to the processor 26a. In some exemplary embodiments, graphical illustrations similar to FIGS. 4A or 4B can be generate and output by the system 10 to characterize a particular aging test.

3. Aspects of the Disclosure

In one aspect, the disclosure is directed to a method of determining settlement characteristics of a drilling mud. The method includes (a) disposing a sample of the drilling mud in an aging cell such that the sample of the drilling mud extends along a vertical axis of the aging cell, (b) imparting a plurality of main pulses of energy to the sample of drilling mud, wherein each of the main pulses of energy is spaced over a testing time interval, (c) recording upper responses and lower responses to the main pulses of energy from respective upper and lower vertical positions along he vertical axis, wherein the upper vertical position is disposed above the lower vertical position, (d) determining that a first upper response and a first lower response recorded at a first response time within the testing interval are generally equivalent, (e) determining that a second upper response and a second lower response recorded at a second response time within the testing interval subsequent to the first response time are generally dissimilar, and (f) estimating a settlement time, based on the first response time and the second response time, at which settlement of heavier elements of the sample of drilling mud settle toward the lower vertical position.

In some exemplary embodiments, the method further includes changing an environmental temperature of the drilling mud along a predetermined schedule for the testing interval and determining a settlement temperature based on the settlement time. In one or more exemplary embodiments, recording upper responses and lower responses comprises recording transducer response signatures from upper and lower transducers supported by the aging cell spaced vertically from one another along the vertical axis.

In some embodiments, imparting the plurality of main pulses of energy to the sample of drilling mud comprises imparting ultrasonic acoustic test pulses to the sample of drilling mud. In one or more exemplary embodiments, recording upper responses and lower responses comprises recording acoustic transducer response signatures from the upper and lower vertical positions. In some embodiments, the method further includes selecting a monitoring window from within a resonance portion of the acoustic transducer response signatures following a main pulse portion of the acoustic transducer response signature, and comparing the acoustic transducer response signatures within the monitoring window to determine that the second upper response and the second lower response are generally dissimilar. In some exemplary embodiments, comparing the acoustic transducer response signatures includes comparing at least one of the group consisting of frequency, propagation speed, wavelength, amplitude power and intensity of the acoustic transducer response signatures.

In another aspect, the disclosure is directed to a method of determining settlement characteristics of a drilling mud that includes (a) disposing a sample of the drilling mud in an aging cell such that the sample of the drilling mud extends along a vertical axis of the aging cell, (b) changing an environmental temperature of the drilling mud along a predetermined schedule over a testing time interval, (c) imparting a plurality of main pulses of energy to the sample of drilling mud, wherein each of the main pulses of energy is spaced over the testing time interval, (d) recording upper responses and lower responses to the main pulses of energy from respective upper and lower vertical positions along the vertical axis, wherein the upper vertical position is disposed above the lower vertical position, and (e) determining a settlement temperature along the predetermined schedule at which settlement of heavier elements of the sample of drilling mud settle toward the lower vertical position by determining a time within the testing time interval at which the upper responses and lower responses recorded generally diverge.

In some exemplary embodiments, the predetermined schedule comprises an initial constant temperature portion and a subsequent increasing temperature portion. In some embodiments, the settlement temperature is determined to be within the increasing temperature portion of the predetermined schedule.

In one or more exemplary embodiments, recording upper responses and lower responses includes recording transducer response signatures from upper and lower transducers supported by the aging cell spaced vertically from one another along the vertical axis. In some embodiments, the method further includes recording intermediate transducer response signatures from one or more intermediate transducers supported by the aging cell spaced vertically between the upper and lower transducers. In some exemplary embodiments, recording upper responses and lower responses includes recording acoustic transducer response signatures from the upper and lower transducers.

In some exemplary embodiments, imparting the plurality of main pulses of energy to the sample of drilling mud comprises imparting the plurality of main pulses from the upper and lower transducers. In one or more exemplary embodiments, the method further includes selecting a monitoring window from within a resonance portion of the acoustic transducer response signatures following a main pulse portion of the acoustic transducer response signatures, and in some embodiments recording upper responses and lower responses to the main pulses comprises recording an ultrasonic parameter of the upper and lower responses from the monitoring window, and in some embodiments the ultrasonic parameter comprises a(least one of the group consisting of frequency, propagation speed, wavelength, amplitude power and intensity. In one or more exemplary embodiments, selecting the monitoring window comprises selecting the monitoring window dependent on an aspect of one or more of the acoustic transducer response signatures.

In still another aspect, the disclosure is directed to a testing system for determining settlement characteristics of a drilling mud. The system includes an aging cell defining a vertical axis therealong, and a plurality of transducers supported by the aging cell and spaced vertically along the vertical axis. The transducers are operable to record responses to main pulses of energy imparted to a sample of drilling mud disposed within the aging cell from respective upper and lower vertical positions along the vertical axis. The system also includes a processor coupled to the plurality of transducers and operable to receive the responses from the plurality of transducers. The processor is operably coupled to a non-transitory memory including instructions thereon to cause the processor to compare the responses from the upper and lower vertical positions, and to determine whether the responses from the upper and lower vertical positions are generally equivalent or generally divergent.

In some embodiments, the plurality of transducers comprises a plurality of ultrasonic transducers. In some exemplary embodiments, the non-transitory memory further includes instructions to cause the plurality of transducers to impart a plurality of main pulses of energy to the sample of drilling mud spaced over a testing time interval. In one or more exemplary embodiments, the system further includes a heater operably coupled to the processor, and in some embodiments, the non-transitory memory further includes instructions to cause the heater to change an environmental temperature of the testing cell along a predetermined schedule.

Moreover, any of the methods described herein may be embodied within a system including electronic processing circuitry to implement any of the methods, or a in a computer-program product including instructions which, when executed by at least one processor, causes the processor to perform any of the methods described herein.

The Abstract of the disclosure is solely for providing the United States Patent and Trademark Office and the public at large with a way by which to determine quickly from a cursory reading the nature and gist of technical disclosure, and it represents solely one or more embodiments.

While various embodiments have been illustrated in detail, the disclosure is not limited to the embodiments shown. Modifications and adaptations of the above embodiments may occur to those skilled in the art. Such modifications and adaptations are in the spirit and scope of the disclosure.

What is claimed is:

1. A method of characterizing settlement characteristics of a drilling mud, the method comprising:
   disposing a sample of the drilling mud in an aging cell such that he sample of the drilling mud extends along a vertical axis of the aging cell;
   imparting a plurality of main pulses of energy to the sample of drilling mud, wherein each of the main pulses of energy is spaced over a testing time interval;
   recording upper responses and lower responses to the main pulses of energy from respective upper and lower vertical positions along the vertical axis, wherein the upper vertical position is disposed above the lower vertical position;
   determining that a first upper response and a first lower response recorded first response time within the testing interval are generally equivalent; and
   determining that a second upper response and a second lower response recorded at a second response time within the testing interval subsequent to the first response time are generally dissimilar; and estimating a settlement time, based on the first response time and the second response time, at which settlement of heavier elements of the sample of drilling mud settle toward the lower vertical position.

2. The method of claim 1, further comprising changing an environmental temperature of the drilling mud along a predetermined schedule for the testing interval and determining a settlement temperature based on the settlement time.

3. The method of claim 1, wherein imparting the plurality of main pulses of energy to the sample of drilling mud comprises imparting acoustic test pulses to the sample of drilling mud.

4. The method of claim 3, wherein recording upper responses and lower responses comprises recording acoustic transducer response signatures received by acoustic transducers disposed at the upper and lower vertical positions.

5. The method of claim 4, further comprising selecting a monitoring window from within a resonance portion of the acoustic transducer response signatures following a main pulse portion of the acoustic transducer response signature, and comparing the acoustic transducer response signatures within the monitoring window to determine that the second upper response and the second lower response are generally dissimilar.

6. The method of claim 5, wherein comparing the acoustic transducer response signatures comprises comparing at least one of the group consisting of frequency, propagation speed, wavelength, amplitude power and intensity of the acoustic transducer response signatures.

7. The method of claim 1, wherein recording upper responses and lower responses comprises recording transducer response signatures received by upper and lower transducers supported by the aging cell spaced vertically from one another along the vertical axis.

8. A method of characterizing settlement characteristics of a drilling mud, the method comprising:
    disposing a sample of the drilling mud in an aging cell such that the sample of the drilling mud extends along a vertical axis of the aging cell;
    changing an environmental temperature of the drilling mud along a predetermined schedule over a testing time interval;
    imparting a plurality of main pulses of energy to the sample of drilling mud, wherein each the main pulses of energy is spaced over the testing time interval;
    recording upper responses and lower responses to the main pulses of energy from respective upper and lower vertical positions along the vertical axis, wherein the upper vertical position is disposed above the lower vertical position; and
    determining a settlement temperature along the predetermined schedule at which settlement of heavier elements of the sample of drilling mud settle toward the lower vertical position by determining a time within the testing time interval at which the upper responses and lower responses recorded generally diverge.

9. The method of claim 8, wherein the predetermined schedule comprises an initial constant temperature portion and a subsequent increasing temperature portion.

10. The method of claim 9, wherein the settlement temperature is determined to be within the increasing temperature portion of the predetermined schedule.

11. The method of claim 8, wherein recording upper responses and lower responses comprises recording transducer response signatures from upper and lower transducers supported by the aging cell spaced vertically from one another along the vertical axis.

12. The method of claim 11, further comprising recording intermediate transducer response signatures from one or more intermediate transducers supported by the aging cell spaced vertically between the upper and lower transducers.

13. The method of claim 11, wherein the upper and lower transducers are acoustic transducers, and wherein recording upper responses and lower responses comprises recording acoustic transducer response signatures from the upper and lower transducers.

14. The method of claim 13, wherein imparting a plurality of main pulses of energy to the sample of drilling mud comprises imparting the plurality of main pulses from the upper and lower transducers.

15. The method of claim 13, further comprising selecting a monitoring window from within a resonance portion of the acoustic transducer response signatures following a main pulse portion of the acoustic transducer response signatures, and wherein recording upper responses and lower responses to the main pulses comprises recording an ultrasonic parameter of the upper and lower responses from the monitoring window, and wherein the ultrasonic parameter comprises at least one of the group consisting of frequency, propagation speed, wavelength, amplitude power and intensity.

16. The method of claim 13, wherein selecting the monitoring window comprises selecting the monitoring window dependent on an aspect of one or more of the acoustic transducer response signatures.

17. A testing system for characterizing settlement characteristics of a drilling mud, the system comprising:
    an aging cell defining a vertical axis therealong;
    a plurality of transducers supported by the aging cell and spaced vertically along the vertical axis, the transducers operable to record responses to main pulses of energy imparted to a sample of drilling mud disposed within the aging cell from respective upper and lower vertical positions along the vertical axis; and
    a processor coupled to the plurality of transducers and operable to receive the responses from the plurality of transducers;
    a heater operably coupled to the processor; and
    a non-transitory memory including instructions thereon to cause the heater to change an environmental temperature of the testing cell along a predetermined schedule including an initial constant temperature portion and a subsequent increasing temperature portion, to cause the processor to receive the responses from the plurality of transducers simultaneous with the increasing temperature portion, to compare the responses from the upper and lower vertical positions, and to determine whether the responses from the upper and lower vertical positions are generally equivalent or generally divergent.

18. The testing system of claim 17, wherein the plurality of transducers comprises a plurality of ultrasonic transducers.

19. The testing system of claim 17, wherein the non-transitory memory further includes instructions to cause the plurality of transducers to impart a plurality of main pulses of energy to the sample of drilling mud spaced over a testing time interval.

* * * * *

UNITED STATES PATENT AND TRADEMARK OFFICE
CERTIFICATE OF CORRECTION

| | |
|---|---|
| PATENT NO. | : 9,719,965 B2 |
| APPLICATION NO. | : 14/907982 |
| DATED | : August 1, 2017 |
| INVENTOR(S) | : Batakrishna Mandel and Shubhajit Ghosh |

It is certified that error appears in the above-identified patent and that said Letters Patent is hereby corrected as shown below:

Column 1, Line 16, change "fluidr" to -- fluids over --

Column 1, Line 37, change "(end" to -- tend --

Column 2, Line 38, change "feature's" to -- feature(s) --

Column 2, Line 56, change "n" to -- in --

Column 3, Line 20, change "tiode" to -- mode --

Column 4, Line 42, change "he" to -- the --

Column 7, Line 8, change "initially" to -- Initially --

Column 7, Line 34, change "o" to -- to --

Column 8, Line 38, change "he" to -- the --

Column 9, Line 62, change "a(least" to -- at least --

Column 10, Line 53, change "he" to -- the --

Column 10, Line 64, change "first" to -- at a first --

Column 11, Line 47, change "each the" to -- each of the --

Signed and Sealed this
Tenth Day of April, 2018

Andrei Iancu
*Director of the United States Patent and Trademark Office*